US00PP33501P3

(12) United States Plant Patent
Post

(10) Patent No.: US PP33,501 P3
(45) Date of Patent: Sep. 21, 2021

(54) ***CHRYSANTHEMUM* PLANT NAMED 'DLFMONE3'**

(50) Latin Name: ***Chrysanthemum* X *morifolium***
Varietal Denomination: DLFMONE3

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/089,730

(22) Filed: Nov. 5, 2020

(65) Prior Publication Data

US 2021/0136980 P1 May 6, 2021

Related U.S. Application Data

(60) Provisional application No. 62/973,983, filed on Nov. 5, 2019.

(51) Int. Cl.
*A01H 5/02* (2018.01)
*A01H 6/14* (2018.01)

(52) U.S. Cl.
USPC ..... Plt./286
CPC ..... *A01H 6/1424* (2018.05)

(58) Field of Classification Search
USPC ..... Plt./263.1, 284, 286
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Chrysanthemum* plant named 'DLFMONE3', characterized by its upright plant habit; vigorous growth habit and rapid growth rate; dark green-colored leaves; uniform and freely flowering habit; strong upright flowering stems with numerous inflorescences; semi-double type inflorescences with quilled purplish red to reddish purple-colored ray florets and yellow green-colored disc florets; relative tolerance to low and high production temperatures; and good postproduction longevity.

2 Drawing Sheets

Figure 1:
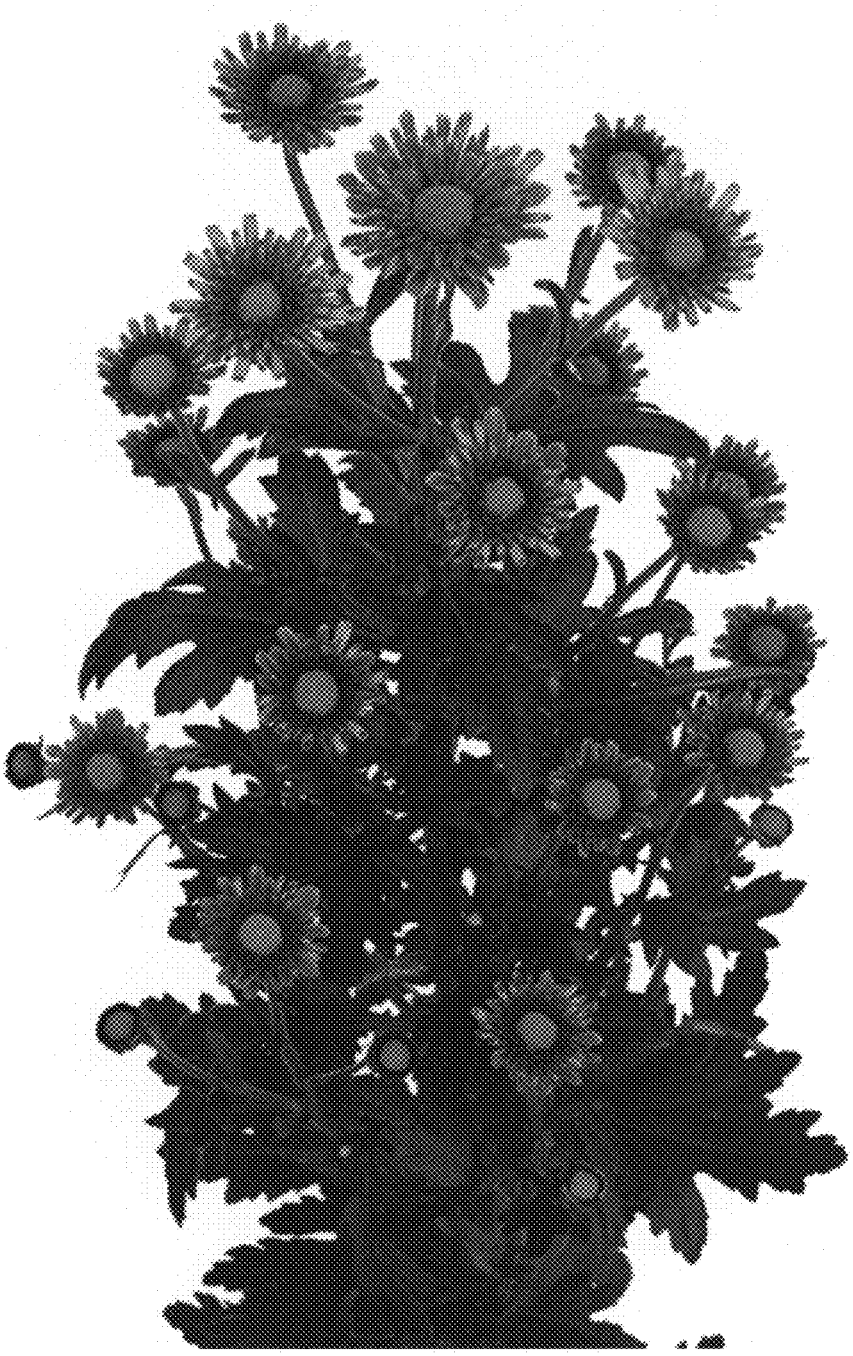
Figure 2:
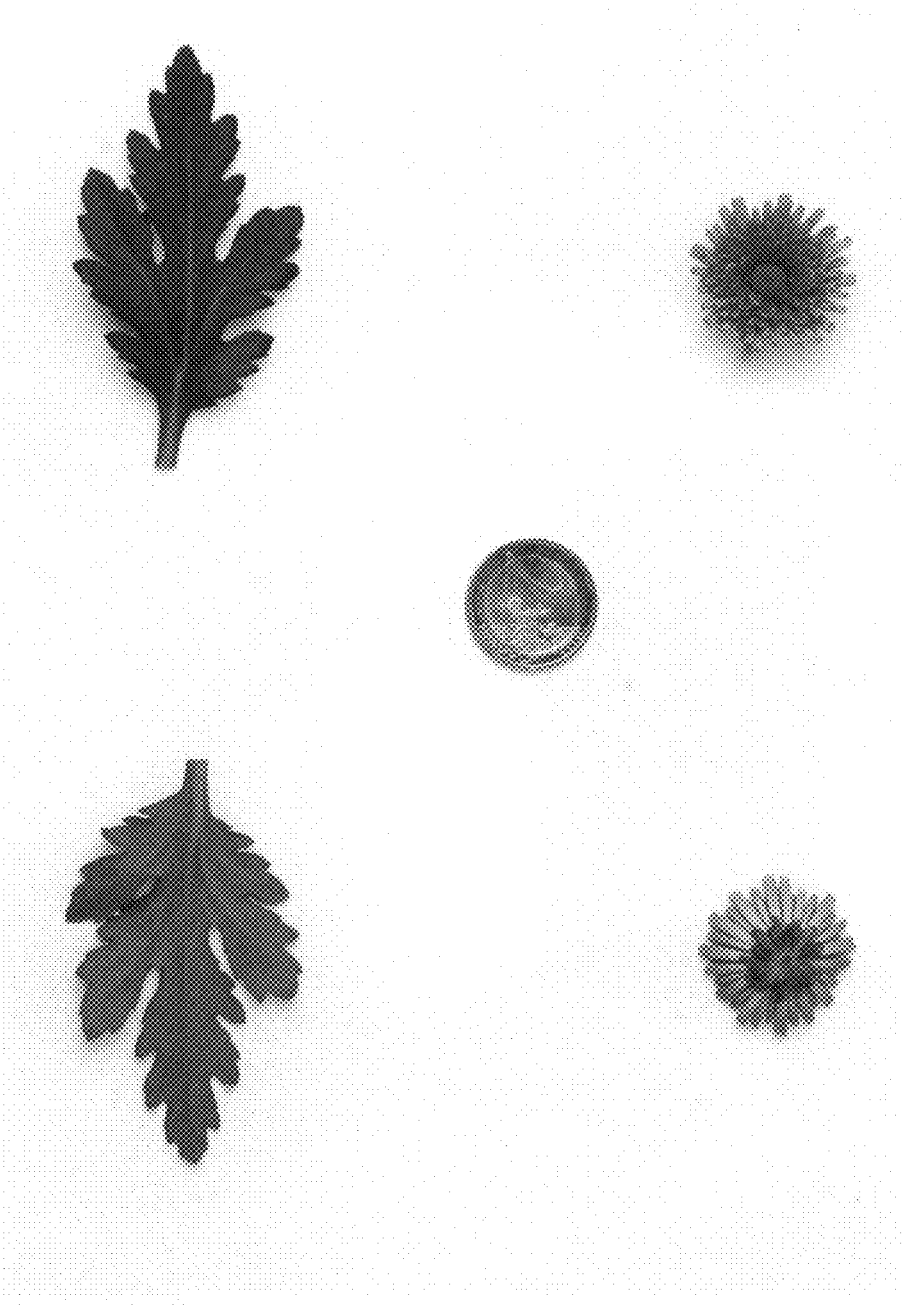

Botanical designation: *Chrysanthemum* X *morifolium*.
Cultivar denomination: 'DLFMONE3'.

CROSS-REFERENCED TO CLOSELY-RELATED APPLICATIONS

Title: Varieties of *Chrysanthemum* Plants
Inventor/Applicant: Arie Gerard Post
Filed: Nov. 5, 2019
Ser. No.: 62/973,983
Inventor/Applicant hereby claim the benefit of this provisional U.S. Patent Application.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFMONE3'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in January, 2009 of a proprietary selection of *Chrysanthemum* x *morifolium* identified as code number db 35211, not patented, as the female, or seed, parent with a proprietary selection of *Chrysanthemum* x *morifolium* identified as code number db 13000, not patented, as the male, or pollen, parent. The new *Chrysanthemum* plant was discovered and selected as a single flowering plant from within the progeny of the stated cross-pollination in a controlled greenhouse environment in Maasdijk, The Netherlands in July, 2010.

Asexual reproduction of the new *Chrysanthemum* plant by vegetative terminal cuttings since July, 2010 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFMONE3'. These characteristics in combination distinguish 'DLFMONE3' as a new and distinct *Chrysanthemum* plant:

1. Upright plant habit.
2. Vigorous growth habit and rapid growth rate.
3. Dark green-colored leaves.
4. Uniform and freely flowering habit.
5. Strong upright flowering stems with numerous inflorescences.
6. Semi-double type inflorescences with quilled purplish red to reddish purple-colored ray florets and yellow green-colored disc florets.
7. Relatively tolerant to low and high production temperatures.
8. Good postproduction longevity.

Plants of the new *Chrysanthemum* differ primarily from plants of the female parent selection in ray floret color as plants of the new *Chrysanthemum* have darker purplish red-colored ray florets than plants of the female parent selection. In addition, plants of the new *Chrysanthemum* have smaller inflorescences than plants of the female parent selection.

Plants of the new *Chrysanthemum* differ primarily from plants of the male parent selection in ray floret color as plants of the new *Chrysanthemum* have darker purplish red-colored ray florets than plants of the male parent selection. In addition, plants of the new *Chrysanthemum* have smaller inflorescences than plants of the male parent selection.

Plants of the new *Chrysanthemum* can be compared to plants of *Chrysanthemum* X *morifolium* 'Delbrestar', not patented. In side-by-side comparisons, plants of the new *Chrysanthemum* differ primarily from plants of 'Delbrestar' in ray floret color as plants of the new *Chrysanthemum* have purplish red to reddish purple-colored ray florets whereas ray florets of 'Delbrestar' are white strongly tinged with purple in color. In addition, plants of the new *Chrysanthemum* have quilled-shaped ray florets whereas than plants of 'Delbrestar' have spatulate-shaped ray florets.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet comprises a side perspective view of a typical flowering stem of 'DLFMONE3' grown as a spray-type cut flower.

The photograph on the second sheet is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFMONE3'.

Parentage:

*Female, or seed, parent*.—Proprietary selection of *Chrysanthemum* x *morifolium* identified as code number db 35211, not patented.

*Male, or pollen, parent*.—Proprietary selection of *Chrysanthemum* x *morifolium* identified as code number db 13000, not patented.

Propagation:

*Type*.—Terminal vegetative cuttings.

*Time to initiate roots, summer*.—About four days at temperatures about 20° C.

*Time to initiate roots, winter*.—About five days at temperatures about 20° C.

*Time to produce a rooted young plant, summer*.—About twelve days at temperatures about 22° C.

*Time to produce a rooted young plant, winter*.—About 14 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous semi-double type cut flower that is typically grown as a single stem spray-type; upright plant habit; vigorous growth habit and rapid growth rate.

*Plant height, soil level to top of foliar plane*.—About 67.7 cm.

*Plant height, soil level to top of inflorescence plane*.—About 74.4 cm.

*Plant (spray) diameter*.—About 13.3 cm.

*Flowering stem length*.—About 67.6 cm.

*Flowering stem diameter*.—About 6 mm.

*Flowering stem internode length*.—About 1.5 cm.

*Flowering stem strength*.—Strong.

*Flowering stem aspect*.—Erect.

*Flowering stem texture and luster*.—Densely pubescent; slightly glossy.

*Flowering stem color, developing*.—Close to 144A.

*Flowering stem color, developed*.—Close to 146C tinged with close to N199A.

*Leaf description*.—Arrangement: Alternate; simple. Length: About 6.8 cm. Width: About 4.2 cm. Shape: Elliptic to obovate. Apex: Abruptly acute. Base: Attenuate. Margin: Palmately lobed, coarsely serrate to dentate; sinuses convergent and medium to deep in depth. Texture and luster, upper surface: Moderately pubescent, not rugose; slightly velvety; very slightly glossy. Texture and luster, lower surface: Moderately pubescent, prominent venation; slightly velvety; matte. Venation pattern: Pinnate, reticulate. Color: Developing leaves, upper surface: Close 137A. Developing leaves, lower surface: Close to between 138B and 147B. Fully developed leaves, upper surface: Darker than between NN137A and 147A; venation, close to 148C. Fully developed leaves, lower surface: Close to 147B; venation, close to 146B. Petioles: Length: About 1 cm. Diameter: About 2 mm by 4 mm. Strength: Moderately strong. Texture and luster, upper and lower surfaces: Moderately to densely pubescent; slightly glossy. Color, upper surface: Close to 147C; edges, darker than NN137A. Color, lower surface: Close to 147C; edges, close to 137B. Stipules: Quantity and appearance: Two leafy stipules, opposite, at the petiole attachment to the stem. Length: About 8 mm. Width: About 9 mm. Shape: Reniform. Texture and luster, upper surface: Moderately pubescent, not rugose; slightly velvety; very slightly glossy. Texture and luster, lower surface: Moderately pubescent, prominent venation; slightly velvety; matte. Color, upper surface: Darker than between NN137A and 147A. Color, lower surface: Close to 147B.

Inflorescence description:

*Appearance*.—Semi-double type inflorescence form with quilled-shaped ray florets and tubular disc florets; inflorescences borne perpendicular to peduncles and face mostly upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 36 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 23 inflorescences develop per flowering stem.

*Inflorescence size*.—Diameter: About 3.7 cm. Depth (height): About 1.2 cm. Disc diameter: About 1.3 cm.

*Receptacles*.—Height: About 4 mm. Diameter: About 6 mm. Shape: Flattened globular. Color: Close to 145A.

*Inflorescence buds*.—Height: About 7 mm. Diameter: About 1.1 cm. Shape: Flattened globular. Texture and luster: Distally, smooth and glabrous; proximally, moderately pubescent; slightly to moderately glossy. Color: Close to 137B, towards the base, 138B; immature ray florets, close to 71A.

*Ray florets*.—Quantity and arrangement: About 120 arranged in about four whorls. Length: About 1.3 cm. Width: About 4 mm. Shape: Quilled; moderately concave and slightly carinate. Apex: Obtuse to shallowly retuse. Base: Fused. Margin: Entire; not undulate. Aspect: Initially upright to about 35° from vertical. Texture and luster, upper surface: Smooth, glabrous; slightly velvety; very slightly glossy. Texture and luster, lower surface: Smooth, glabrous; very slightly velvety; slightly glossy. Color: When opening, upper surface: Close to 70A. When opening, lower surface: Close to 70A to 70B. Fully opened, upper surface: Close to 70B flushed with close to 72D; at the base, close to 157D; venation, similar to lamina colors; color becoming closer to 75A flushed with close to 72D with development. Fully opened, lower surface: Close to between 72D and 75A; at the base, close to 157D; venation, similar to lamina colors; color becoming closer to 75A flushed with close to 76C with development.

*Disc florets*.—Quantity and arrangement: About 200 massed at the center of the receptacle. Length: About 4.5 mm. Diameter: About 1 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Distally, close to 154C; at the apex, close to N144A; and proximally, close to 145C. Color, fully opened, inner and outer surfaces: Distally, close to 151D and proximally, close to 145C.

*Involucral bracts*.—Quantity and arrangement: About 22 arranged in about two whorls. Length: About 9 mm. Width: About 3 mm. Shape: Ovate to narrowly ovate. Apex: Obtuse. Base: Cuneate. Margin: Entire. Texture and luster, upper surface: Smooth, glabrous; glossy. Texture and luster, lower surface: Moderately pubescent; slightly glossy. Color, upper surface: Close to 143A to 143B; margins, translucent and close to 157D and N199A. Color, lower surface: Close to 137A; towards the apex, close to NN137A; margins, translucent and close to 157C and N199A.

*Peduncles*.—Length, terminal peduncle: About 6 cm. Diameter, terminal peduncle: About 2 mm. Length, third peduncle: About 7.9 cm. Diameter, third peduncle: About 2 mm. Strength: Strong. Aspect, terminal peduncle: Mostly upright. Aspect, third peduncle: About 40° from the flowering stem axis. Texture and luster: Densely pubescent; very slightly glossy. Color: Close to between 143A and 144A.

*Reproductive organs*.—Androecium: Present on disc florets only. Quantity: About five per floret. Filament length: About 2 mm. Filament color: Close to 145B. Anther size: About 0.5 mm by 2 mm. Anther shape: Narrowly oblong. Anther color: Close to 12B. Pollen amount: Scarce. Pollen color: Close to 14A. Gynoecium: Present on both ray and disc florets. Quantity: One per floret. Pistil length: About 4 mm. Style length: About 3.5 mm. Style color: Close to N144D. Stigma diameter: About 1 mm. Stigma shape: Cleft, decurrent. Stigma color: Close to 153D. Ovary color: Close to 157C.

*Seeds and fruits*.—To date, seed and fruit production have not been observed on plants of the new *Chrysanthemum*.

Pathogen & pest resistance: To date, plants of the new *Chrysanthemum* have not been observed to be resistant pathogens or pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFMONE3' as illustrated and described.

* * * * *